United States Patent [19]

Bellin et al.

[11] Patent Number: 4,546,776
[45] Date of Patent: Oct. 15, 1985

[54] PORTABLE EKG MONITORING DEVICE FOR ST DEVIATION

[76] Inventors: Howard T. Bellin, 240 E. 47th St., New York, N.Y. 10017; Donald Fellner, 6 E. 74th St., New York, N.Y. 10028; Nichan Tchorbajian, 96-10 23rd Ave., Elmhurst, N.Y. 11373

[21] Appl. No.: 650,108

[22] Filed: Sep. 13, 1984

[51] Int. Cl.⁴ .............................................. A61B 5/04
[52] U.S. Cl. ................................................... 128/704
[58] Field of Search .............................. 128/702–704, 128/706

[56] References Cited

U.S. PATENT DOCUMENTS

| | | | |
|---|---|---|---|
| 3,524,442 | 8/1970 | Horth | 128/703 |
| 3,822,696 | 7/1974 | Ekstrom et al. | 128/703 |
| 3,858,034 | 12/1974 | Anderson | 128/704 |
| 3,868,567 | 2/1975 | Ekstrom | 128/740 |
| 4,083,366 | 4/1978 | Gombrich et al. | 128/690 |

FOREIGN PATENT DOCUMENTS 182849  8/1966  U.S.S.R. .............................. 128/704

Primary Examiner—William E. Kamm
Attorney, Agent, or Firm—Hopgood, Calimafde, Kalil, Blaustein & Judlowe

[57] ABSTRACT

A portable cardiac monitor analyzes the PQ and ST portions of an electrocardiogram waveform and establishes a "normal" or standard ST ratio deviation of the difference between the ST and PQ levels. When a subsequently measured ST ratio deviation exceeds the previously stored normal value, an alarm is indicated indicating a possible ischemic condition. The pulse rate may also be monitored to provide an alarm whenever the pulse rate rises above or falls below a predetermined value.

6 Claims, 6 Drawing Figures

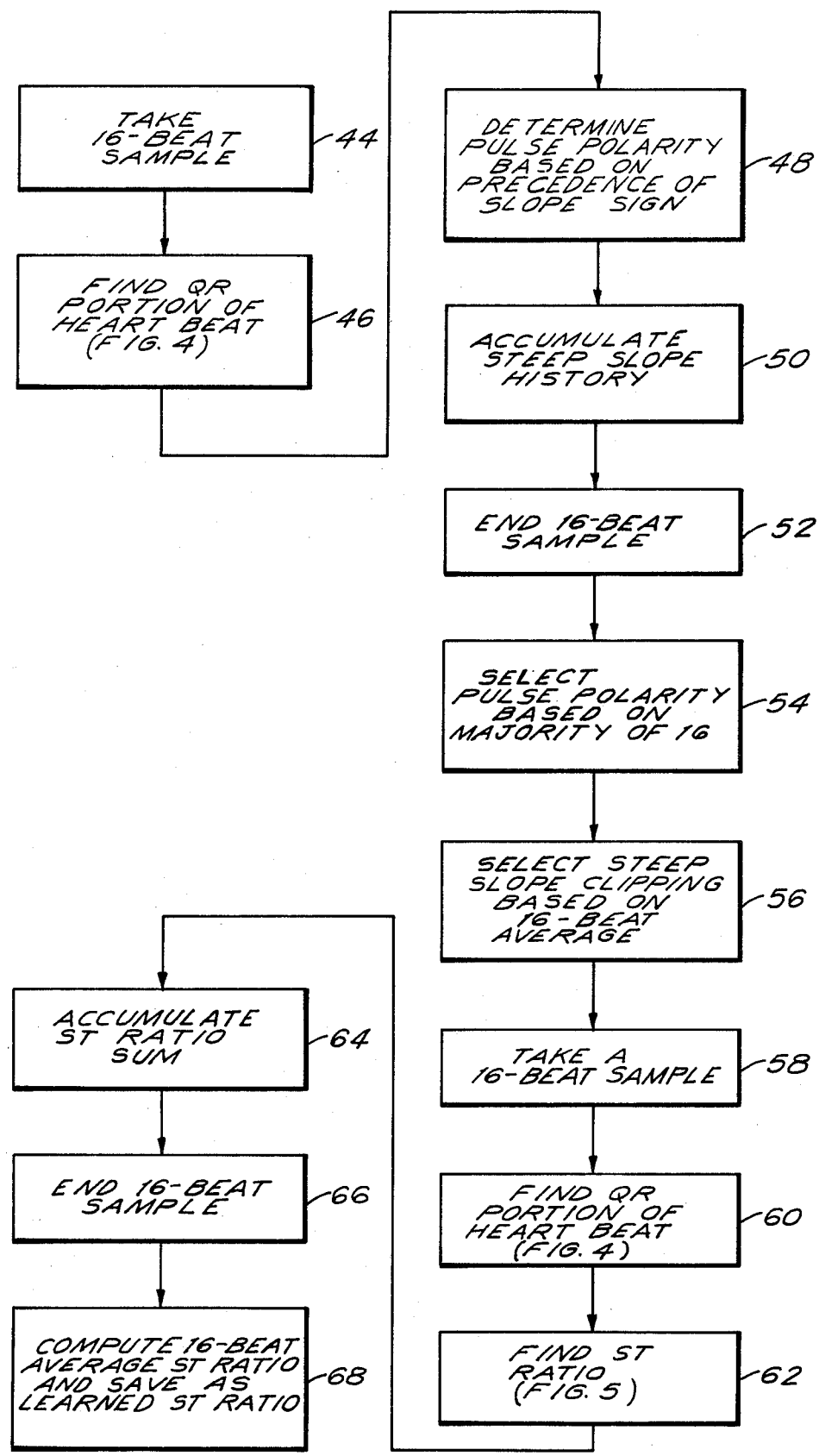
FIG. 3 LEARN MODE

```
┌─────────────────┐
│  DISCRIMINATE   │
│  BEAT BASED     │──70
│  ON STEEP SLOPE │
│  DELTA          │
└────────┬────────┘
         ▼
┌─────────────────┐
│ ELIMINATE WEAKEST│
│ AMPLITUDE PULSE │
│ IF TWO PULSES   │──72
│ OCCUR WITHIN    │
│ 120 MS. OF ONE  │
│ ANOTHER         │
└────────┬────────┘
         ▼
┌─────────────────┐
│ ELIMINATE SPIKES│
│ SHORTER THAN    │──74
│ 20 MS. DURATION │
└────────┬────────┘
         ▼
┌─────────────────┐
│ ACCEPT QR PULSE │
│ ONLY OF LEARNED │──76
│ POLARITY        │
└─────────────────┘
```

FIND QR PORTION OF HEAT BEAT

FIG. 4

```
┌─────────────────┐
│ AFTER FINDING QR,│──78
│ BACK UP TO Q    │
└────────┬────────┘
         ▼
┌─────────────────┐
│ SAMPLE PREVIOUS │
│ 80 MS FOR SLOPE │──80
│ CLOSEST TO ZERO │
└────────┬────────┘
         ▼
┌─────────────────┐
│ USE THIS VOLTAGE│
│ AS THE PQ       │──82
│ VALUE           │
└────────┬────────┘
         ▼
┌─────────────────┐
│ CONTINUE FORWARD│──84
│ FROM QR TO S    │
└────────┬────────┘
         ▼
┌─────────────────┐
│ SAMPLE THE NEXT │
│ 80 MS FOR THE   │──86
│ SLOPE CLOSEST TO│
│ ZERO            │
└────────┬────────┘
         ▼
┌─────────────────┐
│ USE THIS VOLTAGE│──88
│ AS THE ST VALUE │
└────────┬────────┘
         ▼
┌─────────────────┐
│ COMPUTE ST RATIO│
│ AS DIFFERENCE   │
│ BETWEEN ST      │──90
│ VALUE AND PQ    │
│ VALUE           │
└─────────────────┘
```

FIND ST RATIO

FIG. 5

CONSTANT OPERATION-
RUN MODE

PORTABLE EKG MONITORING DEVICE FOR ST DEVIATION

The present invention relates generally to cardiac monitoring devices, and more specifically to a cardiac monitoring device which monitors the ST ratio deviation in an individual's electrocardiogram waveform.

In recent years, as many Americans have become more aware of and concerned with their health and fitness, there has been an increasing awareness of the need for units that can be attached to the body of an individual to monitor the individual's heart condition. For example, an individual such as a jogger who feels a general concern about his or her health may wear such a monitor to warn him or her of an impending cardiac episode, which, if detected early, would greatly enhance the individual's chances of survival and recovery. A cardiac monitor may also be worn by an individual who has had a prior heart attack and who is naturally concerned about the recurrence of a cardiac problem. In addition, a cardiac monitor may be worn by a patient who is undergoing an office procedure such as an endoscopy or by a patient who has been discharged from a cardiac care unit but who is still in a precarious condition while still in the hospital.

A conventional cardiac monitor, such as the one described, for example, in U.S. Pat. No. 3,868,567, monitors an electrocardiogram waveform (EKG), which includes a portion referred to as the QRS complex that results from the depolarization of the ventricles prior to contraction. Immediately preceding the QRS complex is a small wave, referred to as the P wave, which results from the initiation of muscular activity. Following the QRS complex is an additional positive pulse referred to as the T wave.

It is known that the relationship between the amplitude of the ST segment of the electrocardiogram is of significance to the condition of the heart. Thus, an elevation or depression of the ST segment with respect to the earlier PQ segment indicates an insufficient supply of blood being delivered to the heart, a condition known as ischemia. This condition is dangerous and could well be life-threatening if the individual does not receive prompt medical attention. Despite the general knowledge of the relationship between a deviation in the ST level and the oncoming of a potentially serious cardiac event, no portable cardiac monitor has been made available that reliably monitors this factor and reliably provides an indication of a potentially dangerous ischemic condition.

It is a general object of the invention to provide an improved portable cardiac monitor.

It is a further, more specific, object of the invention to provide a portable cardiac monitor which provides a clear and early warning of an ischemic condition by continuously monitoring the ST deviation.

The cardiac monitor of the present invention measures the PQ and ST portions of a patient's normal electrocardiogram waveform and stores a value equal to the difference between the values of these levels as a standard or reference ST deviation. The ST deviation is then continuously measured and compared to the stored standard ST deviation. Whenever the measured ST deviation differs from the stored or normal ST deviation by a predetermined amount, an alarm is sounded to indicate a possibly dangerous heart condition.

To the accomplishment of the above and to such further objects as may hereinafter appear, the present invention relates to a portable cardiac monitor, substantially as defined in the appended claims and as described in the following specification as considered with the attached drawings in which:

FIGS. 3-6 are flow charts of portions of the program implemented in the microprocessor of the portable cardiac monitor of FIG. 2.

Figure 1:
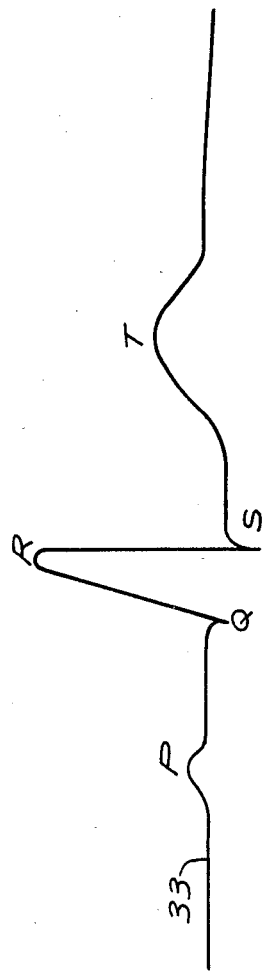
FIG. 1 is a typical electrocardiogram waveform.

The cardiac monitor of the invention analyzes an individual's electrocardiogram waveform and detects deviations in the ST segment against a predetermined and stored reference or normal value. Referring to FIG. 1, a normal adult electrocardiagram waveform (EKG) is illustrated. This waveform includes, in sequence, a P wave of positive polarity, a QRS complex consisting of a negative Q wave, a large positive R wave, a negative S wave, and a T wave separated from the QRS complex. In an actual EKG waveform several additional waves are present but these have no significance to the present invention and have been omitted for purposes of clarity.

The P wave is normally a small positive pulse that corresponds to a body impulse triggering the heartbeat and the resulting reflexive expansion and contraction thereof. Following the P wave is a quiescent portion, the PQ segment, of substantially uniform amplitude. This quiescent PQ segment lasts for approximately 0.04 seconds. At the conclusion of this segment the QRS complex occurs prior to the ventricular contractions producing the actual pumping in the heart.

Following the QRS complex in the T wave, between the S and T waves, is a second, relatively uniform segment, the ST segment. The amplitude of this segment is normally approximately equal to the PQ segment. It has been discovered that under exercise testing the normal amplitude of the ST segment will change. A healthy heart may have a slight depression of the ST segment relative to the PQ segment. A depression of up to approximately 100 microvolts is usually considered normal depending on other factors. Depression or elevation of the ST segment of more than this level is indicative of impending heart damage or other condition which requires prompt medical attention. It warns the user to cease vigorous activity at once.

Figure 2:
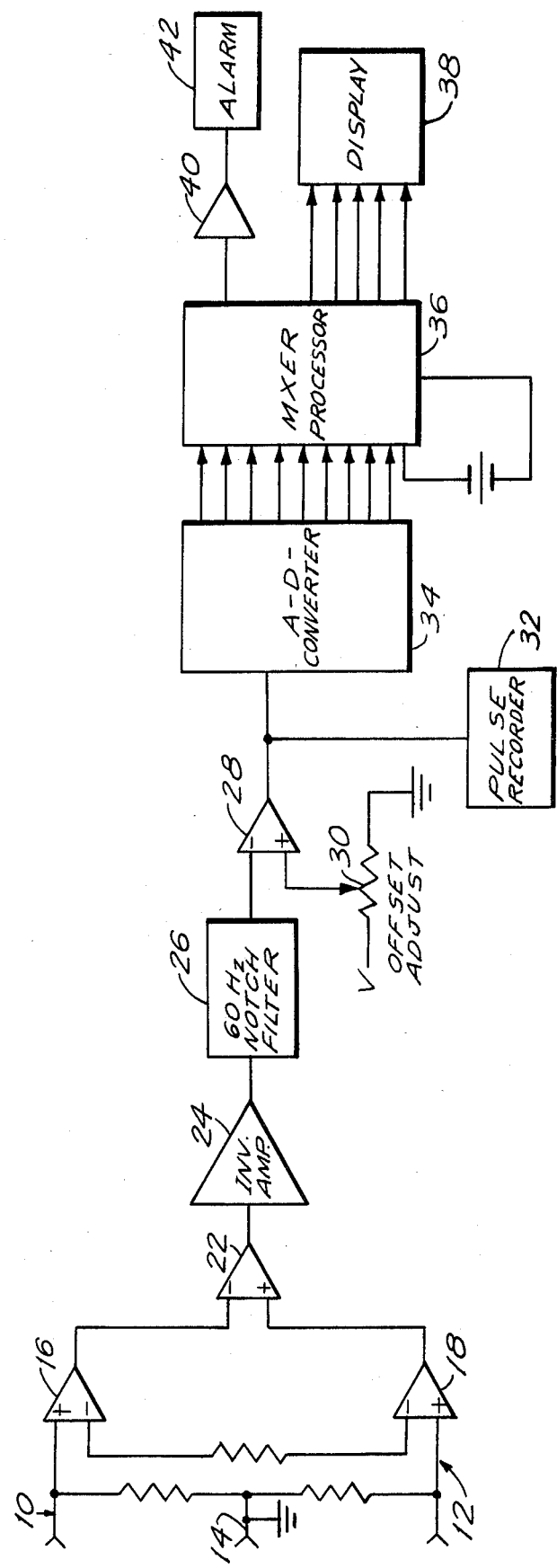
FIG. 2 is an electrical schematic diagram of a portable cardiac monitor in accordance with an embodiment of the invention.

The cardiac monitor of the present invention, an embodiment of which is illustrated in FIG. 2, monitors the ST level as compared to the PQ level of the individual's EKG waveform and sounds an alarm when there has been an excessive change in the ST level. The electronic portion of the cardiac monitor shown in FIG. 2 produces an electrical analog representation of the individual's electrocardiogram waveform and converts it to a corresponding digital signal, which is measured and analyzed in the microprocessor portion of the unit to provide the desired monitoring of the ST deviation in accordance with the program described in the flow charts of FIGS. 3-6.

As shown in FIG. 2, the monitor of the invention includes electrodes 10, 12 and 14 secured to the individual's body with a conductive adhesive as is per se known. Electrode 14 is grounded whereas electrodes 10 and 12 are respectively connected to the inputs of operational amplifiers 16 and 18. The other inputs of amplifiers 16, 18 are connected to one another through a resistor 20 and their outputs are connected to the inputs of an operational amplifier 22. The output of amplifier 22 is applied to an inverter 24 the output of which is applied to the input of a 60 Hz notch filter 26, which filters out 60 Hz noise. The output of filter 26 is applied to one input of a differential amplifier 28, the other input of which is connected to an offset adjust potentiometer 30.

The output of amplifier 28, which is an analog voltage representation of the electrocardiogram waveform of FIG. 1, is applied to a pulse recorder 32 and to the input of an analog-to-digital converter 34 which converts the analog signal into an 8-bit digital signal that is applied to a microprocessor 36. The microprocessor 36 operating in accordance with the program illustrated in FIGS. 3–6, as described in greater detail below, measures the ST and PQ segments of the electrocardiogram waveform and provides data to a display 38. When the deviation of the measured ST segment and the PQ segment differs by a predetermined amount from a stored reference ST deviation signal, a warning signal is produced by the microprocessor, which is amplified in an amplifier 40 and then actuates an alarm 42 to indicate a potentially dangerous ischemic condition in the individual that requires prompt medical attention.

The microprocessor 36 operates initially in accordance with the learn mode illustrated in flow-chart form in FIG. 3 to recognize a valid heart beat for the individual to establish the normal ST deviation for that individual. Once that is completed, the cardiac monitoring unit of the invention is then caused to operate in the constant of run mode illustrated in flow-chart form in FIG. 6 to determine if the measured ST deviation differs from the normal ST deviation by a specified amount and to cause an alarm to be sounded when that occurs.

As shown in FIG. 3, the learn mode is initiated at step 44 at which the microprocessor is instructed to take a 16-beat sample. Thereafter, a subroutine is performed as indicated at 46 to find the QR portion of the heart beat. This subroutine is described in greater detail below with reference to FIG. 4.

Following the completion of subroutine 46, the QR portion is sampled at a rate of, say, 200 times a second, to determine, as shown at step 48, the polarity of the QR pulse based on the precedence of the slope sign. Then, at step 50, a steep slope history of the QR pulse is accumulated in terms of the measured polarities of the slope at the sampled portions of the QR pulse so as to establish the shape of the QR pulse.

Then, at step 52, the 16-beat sample is ended, and at step 54, the actual polarity of the pulse is selected, either + or −, based on the majority of the slope histories taken for the 16-beat sample in the previous steps. In addition, at step 56, the steep slope clipping is selected based on the 16-beat average of the duration or width of the RQ pulse. In steps 44–56 the individual's heart pulse is identified and characterized by slope and duration so that in subsequent analyses of the individual's heartbeat, as described below, a basis for distinguishing noise from a valid heartbeat signal is established.

Following this sequence, at step 58, a second 16-beat sample is taken, and at step 60 the subroutine for finding the QR portion of the heartbeat is again carried out in accordance with the sequence illustrated in FIG. 4. Thereafter, at step 62, a subroutine for finding the ST ratio, that is, the difference between the ST level and the PQ level (see FIG. 1), is determined for each beat in accordance with the sequence illustrated in flow-chart form in FIG. 5.

Thereafter, at step 64, the sum of the ST ratios thus determined is accumulated, and at step 66 the 16-beat sample is ended. To complete the learn mode, at step 68 the 16-beat average of the measured ST ratios is completed and stored as the learned or normal ST ratio.

Figure 6:
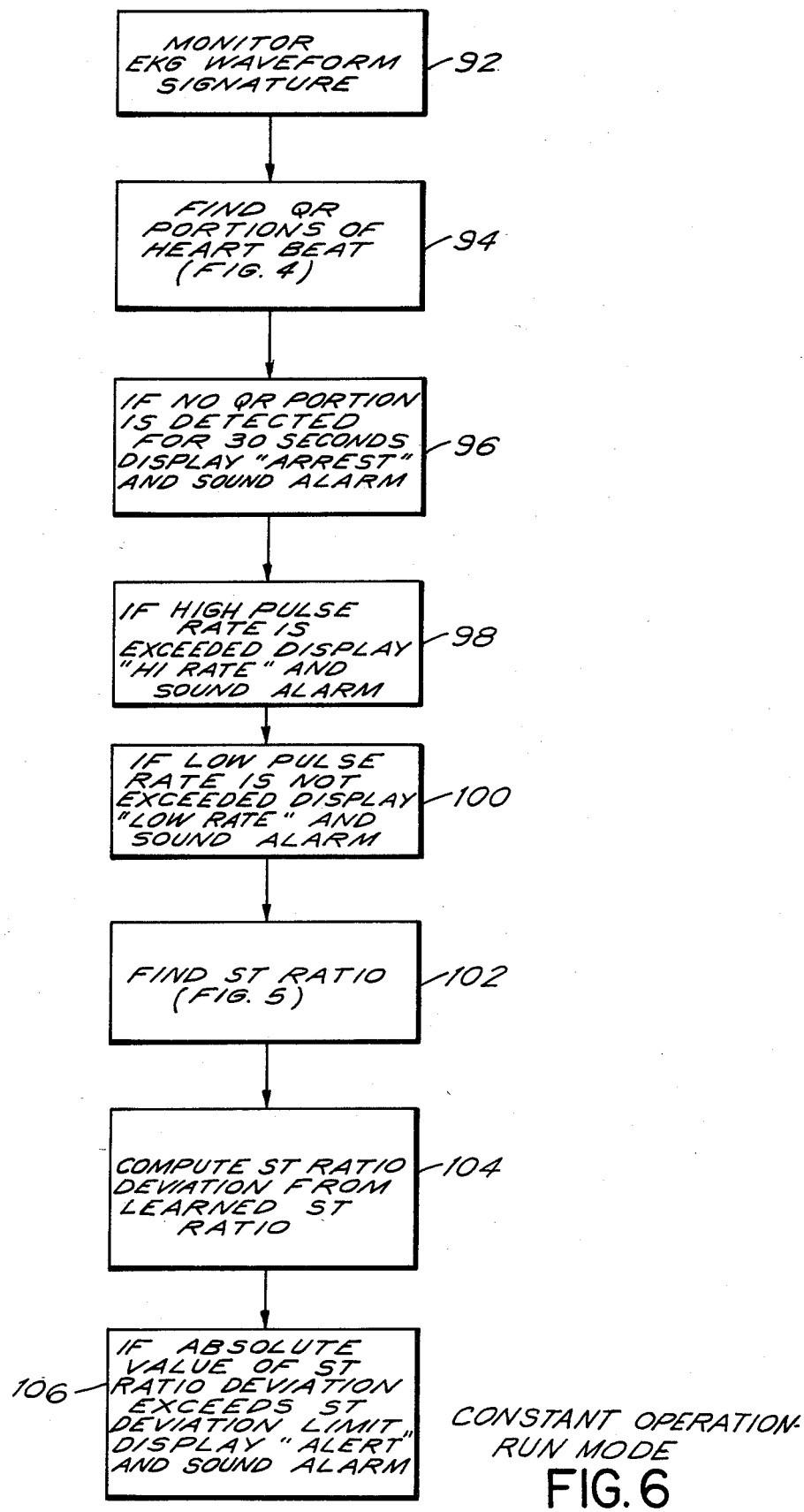

The subroutine indicated as steps 46, 60 of the learn mode, which is also performed during the run mode of FIG. 6, is illustrated in FIG. 4 in which only the first three steps 70, 72, 74 are practiced during the learn mode, the additional step 76 also being performed during the run mode described below with reference to FIG. 6. In step 70 of the find QR subroutine, the various heart beats being processed are discriminated or distinguished based on steep slope delta. In step 70 each beat is classified as zero, plus, or minus based on the sampled slopes of the QR portion of the heart beat. When the sampling produces a series of plus or minus slope measurements, it is then determined that a valid heartbeat rather than a random or noise signal has been detected.

Thereafter, at step 72, the weakest amplitude pulse is eliminated if two pulses are detected as occurring within 120 ms of one another, and at step 74 pulses or spikes of less than 20 ms in duration are also eliminated, thereby to eliminate possible noise pulses. At step 76, which, as noted, is only carried out in the run mode, a QR pulse is accepted only if it is of the learned polarity determined at step 70.

The ST ratio subroutine carried out at step 62 in the learn mode program, as illustrated in FIG. 5, begins at step 78 by backing up in the detected heartbeat to point Q (FIG. 1) after the QR portion of the pulse has been found in the QR subroutine of FIG. 4. Thereafter, at step 80, the prior 80 ms period is sampled at a predetermined rate of say 200 times per second. The slope is measured at the sampled points and the measured slope closest to zero is determined. The voltage level at the point of minimum slope is then used as the PQ value as shown at step 82.

Then, at step 86, the following 80 ms period is sampled and again the point at which slope is nearest to zero is determined. The measured voltage at this point is used as the ST value as shown at step 88. From the voltage values obtained at steps 82 and 88, the ST ratio voltage level is computed at step 90 as the difference between the measured ST and PQ voltage values.

Once the learn mode is completed and the normal or learned ST ratio is derived and stored in the manner described, the run mode illustrated in FIG. 6 is performed in a continuous manner to monitor any possible deviations in the individual's ST ratio which would indicate a dangerous and possibly life-threatening cardiac situation. In the run mode, the individual's EKG waveform signature is continuously monitored at step 92 and the QR portion of the heart beat is found at step 94 in accordance with the subroutine illustrated in FIG. 4.

If no QR portion is detected at step 94, for a period of say 30 seconds, an "arrest" signal is displayed and an alarm is sounded as shown at step 96. Preferably the microprocessor also measures the pulse rate or the number of heartbeats per minute, and at steps 98 and 100, respectively, if the measured pulse rate either exceeds or is below a preset pulse rate, an appropriate "hi rate" or "lo rate" indication is given and an alarm is sounded.

Thereafter the run mode program, at step 102, executes the ST ratio subroutine illustrated in FIG. 5 and the difference or deviation between the thus measured ST ratio and the learned or normal ST ratio derived during the learn mode is computed at step 104. If the computed value of the deviation of the measured ST ratio from the learned ST ratio exceeds a preset limit, an "Alert" display is activated and an alarm is sounded to indicate a potentially dangerous ischemic condition.

It will thus be appreciated that the cardiac monitor of the present invention has the capability of continuously monitoring an individual's electrocardiogram waveform to detect, and activate an alarm upon, the occurrence of any dangerous deviation in the ST ratio. It will also be appreciated that modifications and variations may be apparent to those skilled in the art to the embodiment of the invention hereinabove described without necessarily departing from the spirit and scope of the invention.

What is claimed is:

1. A cardiac monitoring unit comprising sensing means adapted to be attached to the body of an individual to produce an analog representation of the individual's electrocardiogram waveform; means coupled to said sensing means for establishing and storing an ST deviation signal corresponding to the ST deviation of said electrocardiogram waveform; said ST deviation signal establishing means comprising means for locating the QR portion of the waveform, means for sampling a first portion of the waveform at a predetermined period prior to the Q portion of the waveform, means for measuring the slope of the waveform at the sampled points in said first portion, means for determining a first voltage of the waveform at which the measured slope is nearest to zero, means for sampling a second portion of the waveform at a predetermined period subsequent to the S portion of the waveform, means for measuring the slope of the waveform at the sampled points in said second portion, means for determining a second voltage of said second portion of the waveform at which the measured slope is nearest to zero, and means for determining the ST deviation signal as the difference between said first and second voltages; means for thereafter continuously monitoring the ST deviation signal of said electrocardiogram waveform and for comparing the monitored ST deviation signal with the stored normal ST deviation signal; and means for activating an alarm when the monitored ST deviation signal bears a predetermined relation to the stored normal ST deviation signal.

2. The cardiac monitoring device of claim 1, further comprising means coupled to said sensing means for converting said analog representation to a corresponding digital signal, and a microprocessor including said establishing and storing means and said comparing means coupled to said converting means.

3. The cardiac monitoring device of claim 2, in which said microprocessor further comprises means for identifying and characterizing a normal heartbeat shape for the individual from said electrocardiogram waveform.

4. The cardiac monitoring device of claim 1, further comprising means for actuating an alarm whenever the rate of sensed heartbeats exceeds or is lower than a predetermined rate.

5. A method for monitoring an individual's cardiac condition comprising the steps of:
   (a) sensing the individual's electrocardiogram waveform;
   (b) providing an analog voltage representative of said electrocardiogram waveform, said step of establishing said standard ST deviation value comprising the steps of (i) locating the QR portion of the waveform, (ii) sampling a first portion of the waveform at a predetermined period prior to the Q portion of the waveform, (iii) measuring the waveform at the sampled points of said first portion, (iv) determining a first voltage of said first portion of the waveform at which the measured slope is nearest to zero, (v) sampling a second portion of the waveform at a predetermined period subsequent to the S portion of the waveform, (vi) measuring the scope of the waveform at the sampled points of said second portion; (vi) determining a second voltage of said second portion at which the slope is closest to zero, and (viii) determining the ST deviation signal as the difference between said first and second voltages;
   (c) said deviation evaluation step including the steps of establishing a standard ST deviation value for said electrocardiogram waveform;
   (d) storing said standard ST deviation value;
   (e) thereafter continuously measuring the ST deviation value of the individual's electrocardiogram waveform;
   (f) comparing the measured ST deviation value with said standard ST deviation value; and
   (g) actuating an alarm whenever the measured ST deviation value bears a predetermined relationship to said standard ST deviation value.

6. The method of claim 5, further comprising the step of identifying and characterizing a normal heartbeat of the individual.

* * * * *